United States Patent [19]

Souma et al.

[11] Patent Number: 5,091,010
[45] Date of Patent: Feb. 25, 1992

[54] CHROMATIC-COLOR METAL FLAKE PIGMENT AND COLORED COMPOSITION COMPOUNDED THEREWITH

[75] Inventors: Thoru Souma; Masahiro Ishidoya, both of Yokohama; Toshihiko Nakamichi, Fujisawa; Naoe Takai, Tokyo, all of Japan

[73] Assignee: Nippon Oil and Fats Company, Limited, Tokyo, Japan

[21] Appl. No.: 714,313

[22] Filed: Jun. 10, 1991

Related U.S. Application Data

[63] Continuation-in-part of Ser. No. 300,613, Jan. 23, 1989, abandoned.

[30] Foreign Application Priority Data

Jan. 27, 1988 [JP] Japan ................... 63-16657
Dec. 27, 1988 [JP] Japan ................. 63-319246

[51] Int. Cl.$^5$ ................................. C09C 1/62
[52] U.S. Cl. .................... 106/403; 106/404
[58] Field of Search ................. 106/403, 404

[56] References Cited

U.S. PATENT DOCUMENTS

| | | | |
|---|---|---|---|
| 2,768,909 | 10/1956 | Haslam | 117/121 |
| 2,943,955 | 7/1960 | Brill | 117/121 |
| 3,199,999 | 8/1965 | Greening et al. | 106/403 |
| 3,341,291 | 9/1967 | Mubbs et al. | 106/403 |
| 3,440,075 | 4/1969 | Marshall | 106/403 |
| 3,536,520 | 10/1970 | Marshall | 106/403 |
| 3,553,001 | 1/1971 | Kohlschutter | 117/100 |
| 3,862,297 | 1/1975 | Claridge et al. | 106/403 |
| 4,318,747 | 3/1982 | Ishijima et al. | 106/403 |
| 4,622,073 | 11/1986 | Hashizume | 106/403 |
| 4,762,568 | 8/1988 | Nakamura et al. | 106/404 |

FOREIGN PATENT DOCUMENTS

| | | | |
|---|---|---|---|
| 351932 | 1/1990 | European Pat. Off. | 106/403 |
| 53-77225 | 7/1978 | Japan | 106/404 |
| 61-118461 | 6/1986 | Japan | 106/403 |
| 1237866 | 6/1971 | United Kingdom | 106/404 |

*Primary Examiner*—John Zimmerman
*Attorney, Agent, or Firm*—Frishauf, Holtz, Goodman & Woodward

[57] ABSTRACT

A titanium oxide-coated chromatic-color metal flake pigment is prepared by hydrolyzing an organic titanate ester compound, e.g., tetraisopropoxy titanium, in the presence of the base metal flakes suspended in an organic medium having a pH of 4 to 8. The pigment exhibits iridescent color tones of great aesthetic value delicately varying depending on the thickness of the titanium oxide coating layer. The pigment has high chemical stability, for example, against acids, by virtue of the very uniform and dense coating layer of titanium oxide so that the inventive pigment is useful as a coloring agent in a water-borne composition. Application fields of the inventive pigment include colored coating compositions, ink compositions, cosmetic preparations, molding compounds of plastic resins and so on.

14 Claims, No Drawings

CHROMATIC-COLOR METAL FLAKE PIGMENT AND COLORED COMPOSITION COMPOUNDED THEREWITH

This application is a continuation-in-part of application Ser. No. 07/300,613, filed Jan. 23, 1991, now abandoned.

BACKGROUND OF THE INVENTION

1. Field of the Invention

The present invention relates to a novel chromatic-color metal flake pigment and a method for the preparation thereof as well as a colored composition, such as coating compositions, inks, cosmetic preparations and molding compounds of plastic resins, compounded with such a chromatic-color pigment. More particularly, the invention relates to a chromatic-color metal flake pigment of which each metal flake is provided on the surface with a coating layer of titanium oxide and an efficient method for the preparation of such a pigment, as well as a colored composition of high aesthetic value compounded with such a pigment such as coating compositions or paints, ink compositions, cosmetic preparations, molding compounds of plastic resins and the like.

It is known in the art of coating compositions, inks, cosmetic preparations, molding compounds of plastic resins and the like to compound the compositions with metal flake pigments of metal selected from the group consisting of aluminum, bronze, stainless steel, tin, and iron, organic pigments, inorganic pigments, dyes, or pearlescent pigments prepared by forming a coating layer of titanium dioxide on the surface of mica flakes as a material capable of giving high aesthetic value to the composition. These pigments and dyes are used either singly or as a combination of two kinds or more in accordance with the need to obtain a specific highly aesthetic effect of coloring.

Along with the trend in recent years to desire to have various products capable of giving an impression of a personalized high-class product in appearance, consumers' demand is directed toward a novel aesthetic value which can never be obtained with the above mentioned coloring or colored materials. For example, a highly aesthetic coloring effect capable of giving an impression of high-class goods with a silky appearance is desired of which the impression of color received by a viewer is subject to delicate change depending on the angle of incident light and the view angle with reduced glaringness inherent in conventional metal flake pigments.

Several proposals have been hitherto made for novel coloring materials to meet the above mentioned desire. For example, Japanese Patent Kokai 59-126468 and 61-225264 propose a chromatic-color pearlescent pigment of which mica flakes are provided with successive two coating layers of, one, a lower oxide of titanium and, the other, titanium dioxide and a coating composition compounded with such a chromatic-color pearlescent pigment. Japanese Patent Kokai 51-150532 proposes a colored aluminum pigment prepared by providing flakes of metallic aluminum with a coating layer of a hydroxide of metal such as iron and the like.

Though having a higher hiding power than conventional pearlescent pigments, the above mentioned mica-based chromatic pearlescent pigment has a problem in the relatively low weatherability so that this pigment cannot be used in applications in which long-term weatherability is essential as in the field of coating compositions. The colored aluminum pigment above mentioned is also defective in respect of the weatherability and does not always give a quite satisfactory result when it is used as a coloring agent of a coating composition of which long-term weatherability is essential.

SUMMARY OF THE INVENTION

In view of the above described problems and disadvantages in the conventional coloring and colored materials, the present invention has been completed with an object to provide a novel chromatic-color metal flake pigment having excellent general properties as a pigment such as high hiding power, weatherability, resistance against chemicals and the like and capable of expressing a highly aesthetic coloring effect not obtained with any conventional pigment such as an elegant luster with silkiness to give an impression of high-class goods and a method for the preparation of such a pigment, as well as a colored composition compounded with the chromatic-color metal flake pigment such as coating compositions, ink compositions, cosmetic preparations, molding compounds of plastic resins and the like.

Thus, the present invention provides a chromatic-color metal flake pigment of which the metal flakes are provided on the surface with a coating layer of a titanium oxide deposited by the hydrolysis of a hydrolyzable organic titanate ester.

The above defined chromatic-color metal flake pigment of the invention can be prepared by hydrolyzing, in an organic medium at a pH of 4 to 8 containing metal flakes dispersed therein, a hydrolyzable organic titanate ester represented by the general formula $$R—O—[Ti(OR)_2—O]_nR, \qquad (I)$$

in which R is an alkyl group having 2 to 10 carbon atoms and the subscript n is a positive integer not exceeding 10, to deposit an oxide of titanium on the surface of the metal flakes.

DETAILED DESCRIPTION OF THE PREFERRED EMBODIMENTS

With an object to achieve the above mentioned object, the inventors have conducted extensive investigations and, as a result, arrived at a discovery that a chromatic-color metal flake pigment capable of expressing a highly aesthetic coloring effect with a silky luster to give an impression of high-class goods can be obtained when metal flakes are provided on the surface with a coating layer of titanium oxide deposited by the hydrolysis of a hydrolyzable organic titanate ester under specific conditions.

Several methods are known in the prior art for forming a coating layer of a titanium oxide on the surface of a substrate material by the hydrolysis of an inorganic titanium salt such as titanyl sulfate and others disclosed in Japanese Patent Publications 43-25644 and 49-3824 and elsewhere. These prior art methods have a problem that, since the hydrolysis of the inorganic titanium salt is performed in a strongly acidic aqueous medium having a pH of 3 or below, the method is not applicable to metal flakes as the substrate material because the metal flakes are dissolved in the acidic aqueous medium.

The very scope of the present invention accordingly is based on the novel discovery that the above mentioned problem can be solved by providing metal flakes with a uniform coating layer of a titanium oxide on the surface deposited by the hydrolysis of a specific organic titanate ester in an organic medium having a pH of 4 to 8 without causing dissolution of the metal flakes in the medium.

Further, it was found that, when the thus prepared chromatic-color metal flake pigment was compounded as a coloring agent with various kinds of compositions such as coating compositions, ink compositions, cosmetic preparations, molding compounds of plastic resins and the like, the composition gives an impression of color delicately changing depending on the angle of incident light and the view angle to exhibit a highly aesthetic coloring effect with silky appearance of high-class goods and with reduced glaringness as compared with conventional metal flake pigments leading to completion of the present invention.

The metal flakes used as the base material of the inventive chromatic-color metal flake pigment include flakes of a metal such as aluminum, titanium, bronze, stainless steel, tin, iron and the like though not particularly limited thereto. The metal flakes each have a flat configuration of which the average particle diameter within the flat surface is preferably in the range from 1 to 100 μm and the thickness is preferably in the range from 0.01 to 20 μm. Various commercial products of metal flakes are available which satisfy these requirements in the dimensions of the flakes. The metal flakes may have a surface optionally treated with a coupling agent.

When the metal flakes have a particle diameter smaller than 1 μm, the pigment cannot exhibit the characteristics as a metal flake pigment due to the unduly small surface area of the individual flakes available for reflection of light. Metal flakes having an excessively large particle diameter are undesirable because, when such a pigment is compounded with various compositions such as coating compositions, ink compositions, cosmetic preparations and molding compounds of plastic resins, separation of the pigment from the matrix may eventually take place during storage of the composition and coating compositions and ink compositions compounded therewith may have poor workability for coating and printing works. When the thickness of the metal flakes is too small, the flakes may have an unduly low mechanical strength and may be subject to further comminution during processing. When the thickness of the flakes is too large, the pigment may lose the characteristics of flat flaky particles along with a decrease in the workability of the compositions compounded therewith such as coating compositions.

The chromatic-color metal flake pigment of the invention is prepared by hydrolyzing a hydrolyzable organic titanate ester compound in the presence of the above described metal flakes so as to deposit an oxide of titanium on the surface of the flakes in the form of a uniform coating layer. The hydrolyzable organic titanate ester compound above mentioned is a compound represented by the general formula

R—O—$[$Ti(OR)$_2$—O$]_n$—R,     (I)

in which each symbol has the meaning defined before, and this compound is hydrolyzed in an organic medium having a pH of 4 to 8 in the presence of the metal flakes so that an oxide of titanium is deposited on the surface of the metal flakes to form a uniform coating layer.

Examples of the hydrolyzable organic titanate ester compound expressed by the above given general formula (I) of which the subscript n has a value of 1 include tetraisopropoxy titanium, tetra-n-butoxy titanium, tetrakis(2-ethylhexoxy) titanium, tetra-n-pentoxy titanium, tetra-n-hexoxy titanium, tetra-n-heptoxy titanium, tetra-n-octoxy titanium and the like. Partial hydrolysis-condensation products of these titanate esters are also expressed by the same general formula (I) and can be used in the inventive method when the subscript n has a value not exceeding 10. It is optional according to need that the organic titanate ester is cohydrolyzed with an alkoxide of a different metal such as aluminum, zirconium, iron, tin, copper and the like.

Examples of the organic solvents as the organic medium in which hydrolysis of the organic titanate ester compound is performed include monohydric lower alcohols having 1 to 6 carbon atoms in a molecule, e.g., methyl, ethyl, n-propyl, isopropyl, n-butyl, sec-butyl, isobutyl, n-pentyl and n-hexyl alcohols, and aromatic hydrocarbon solvents, e.g., benzene, toluene and xylene, though not particularly limitative thereto. These organic solvents can be used either singly or as a mixture of two kinds or more according to need. These organic solvents are each a good solvent of the above described organic titanate ester compound to form a homogeneous solution in which the hydrolysis reaction of the titanate proceeds smoothly to deposit a uniform coating layer of a titanium oxide on the surface of the metal flakes. It is also optional that the above mentioned organic solvents are combined with other kinds of organic solvents in such a limited proportion that the organic titanate ester can be completely dissolved in the solvent mixture to form a homogeneous solution.

In the following, an example is given of a preferable procedure for practicing the method of the invention for the preparation of the chromatic-color metal flake pigment. In the first place, a suitable amount of the metal flake is added to the above mentioned organic solvent and agitated to form a suspension of the flakes to which water is added. Thereafter, a mixture of a suitable amount of the hydrolyzable organic titanate ester compound and an organic solvent is added dropwise to the suspension of the metal flakes having a pH of 4 to 8 so as to effect hydrolysis of the organic titanate ester and deposit an oxide of titanium on the surface of the metal flakes in the form of a uniform coating layer. This procedure is preferred to an alternative procedure in which the organic titanate ester compound is dissolved in the suspension of the metal flakes in an organic solvent and water or a mixture of water and an organic solvent is added dropwise to the titanate-containing suspension of the metal flakes to effect hydrolysis of the organic titanate ester compound. In the next place, the metal flakes coated on the surface with the titanium oxide are separated from the medium by a known means of solid-liquid separation such as filtration and centrifugal separation and the thus recovered metal flakes are dried and calcined in an atmosphere of an inert gas such as nitrogen and argon to give the desired chromatic-color metal flake pigment of the invention.

The concentration of the organic titanate ester compound to be hydrolyzed in an organic medium is in the range from 0.001 to 1 mole or, preferably, from 0.005 to 0.5 mole per liter of the medium. When the concentration thereof is too low, the volume of the reaction mixture to be handled is so large in order to obtain a desired amount of titanium oxide deposition that the process is practically disadvantageous. An excessively high concentration thereof, on the other hand, is undesirable due to undue growth of the particles of titanium oxide produced by the hydrolysis to cause a decrease in the uniformity of the coating layer.

The value of pH of the reaction mixture is essentially in the range from 4 to 8 in the course of the hydrolysis reaction of the organic titanate ester compound. When the mixture has a value of pH lower than 4 or higher than 8, corrosion or dissolution of the metal flakes may take place in the medium.

The hydrolysis reaction of the organic titanate ester compound is performed at a temperature usually in the range from 15° to 80° C. When the temperature is too low, the hydrolysis reaction is completed by taking an unduly long time to cause a practical disadvantage. A reaction temperature higher than the above mentioned upper limit is undesirable, on the other hand, due to undue growth of the titanium oxide particles produced by the hydrolysis not to give a uniform coating layer on the surface of metal flakes.

The amount of water added to the reaction mixture to effect hydrolysis of the organic titanate ester compound should be at least 2 moles per mole of the organic titanate ester compound. When the amount of water is too small, the hydrolysis reaction of the titanate cannot proceed completely.

The rate of the dropwise addition of the organic titanate ester compound is also an important parameter to ensure uniformity of the coating layer on the metal flakes. Preferably, the rate of addition thereof is in the range from $1.0 \times 10^{-7}$ to $1.0 \times 10^{-4}$ mole per minute per square meter of the surface area of the metal flakes. When the rate of addition is too low, an unduly long time is taken for completion of the reaction to cause a practical disadvantage. When the rate of addition is too high, on the other hand, titanium oxide is produced by the hydrolysis at an unduly high rate not to ensure uniform deposition thereof on the surface of the metal flakes and a considerable fraction thereof may be suspended in the medium without being deposited on the metal flakes.

In an alternative procedure in which water is added dropwise to a suspension of the metal flakes in a non-aqueous medium containing the organic titanate ester compound dissolved therein, the rate of dropwise addition of water is an important parameter to obtain a satisfactory product of the chromatic-color metal flake pigment and it should be in the range from $1.0 \times 10^{-3}$ to 1.0 mole per minute per mole of the organic titanate ester compound. When the rate of addition of water is too low, un unduly long time is taken for completion of the hydrolysis reaction to cause a practical disadvantage. When the rate of addition of water is too high, on the other hand, a disadvantageous increase is caused in the amount of the undeposited titanium oxide particles.

The chromatic-color metal flake pigment of the invention is prepared by separating the metal flakes uniformly coated with a coating layer of titanium oxide in the above described manner from the reaction medium and then drying and calcining the metal flakes in an atmosphere of an inert gas. The calcination is performed at a temperature of 200° C. or higher or, preferably, 300° C. or higher but not exceeding the melting point of the metal flakes. When the temperature of calcination is too low, the titanium oxide forming the coating layer is at least partly left in a hydrated state so that the pigment has poor water resistance. When the temperature of calcination exceeds the melting point of the metal of the flakes, the metal flakes are melted down as a matter of course so that a product in the form of a pigment cannot be obtained.

The colored appearance of the chromatic-color metal flake pigment of the invention can be varied depending on the geometrical thickness of the coating layer of titanium oxide formed in the above described manner. This phenomenon is caused by the interference of light in the coating layer. For example, the inventive pigment has different colors of golden, red, blue and green when the coating layer of titanium oxide on the base metal flake has a thickness in the range from 40 to 90 nm, from 90 to 110 nm, from 110 to 135 nm and from 135 to 155 nm, respectively although a chromatic effect can be obtained even when the thickness of the coating layer is outside of the above mentioned range by the interference of light. The metal of the base flakes, which may be aluminum, titanium, stainless steel, tin, iron or the like, has little influence on the above mentioned relationship between the thickness of the coating layer and the color tone exhibited by the inventive pigment having the coating layer on the surface of the metal flakes although somewhat yellowish tint is exhibited when bronze flakes are used as the base of the inventive pigment.

In the following, descriptions are given of the compositions compounded with the above described chromatic-color metal flake pigment of the invention starting with coating compositions or paints.

A coating composition according to the invention is compounded with the above described chromatic-color metal flake pigment in an amount in the range from 0.1 to 70% by weight based on the film-forming constituent or vehicle therein. The film-forming vehicle of the inventive coating composition is not particularly limitative and any one of conventional resins can be used according to the intended application of the inventive coating composition. Examples of suitable film-forming vehicle resins include synthetic resins such as acrylic resins, polyester resins, resin mixtures of an acrylic resin and cellulose acetate butyrate referred to as CAB hereinbelow, CAB-grafted acrylic resins, alkyd resins, urethane resins, epoxy resins, silicone resins, polyamide resins, epoxy-modified alkyd resins, phenolic resins and the like as well as various kinds of natural resins and cellulose derivatives. These film-forming vehicle resins can be used either singly or as a combination of two kinds or more according to need. If necessary, the above named film-forming vehicle resins are used as combined with a curing agent such as melamine resins, isocyanate compounds, isocyanate compounds having a block-wise structure, polyamine compounds and the like.

The coating composition of the invention essentially contain the chromatic-color metal flake pigment in an amount in the range from 0.1 to 70% by weight based on the above mentioned film-forming vehicle resin. When the amount of the pigment is smaller than 0.1% by weight, the desired effect of aesthetic coloring cannot be obtained. When the amount of the pigment exceeds 70% by weight, on the other hand, no practically useful coating composition can be obtained due to the poor workability of the composition in coating works and poor mechanical properties of the coating films formed therefrom. It is optional in the inventive coating composition that the chromatic-color metal flake pigment is used in combination with other colored pigments conventionally used in coating compositions according to need to further enhance the aesthetic coloring effect.

In addition to the above described film-forming vehicle resins, chromatic-color metal flake pigments and colored pigments of other types optionally added to the composition, the coating composition of the invention can be admixed with various kinds of additives conventionally used in coating compositions including, for example, surface conditioning agents, photostabilizers, antioxidants and the like according to need.

Further, the type of the inventive coating composition is not particularly limitative including the types of a solution in an organic solvent, aqueous solution, powder and emulsion. The process for film-forming of the inventive coating composition can be performed by drying at room temperature, curing by baking and curing by the irradiation with ultraviolet light or electron beams without particular limitations.

When the inventive coating composition is of the type of a solution in an organic solvent, the solvent suitable therefor is not particularly limitative including those organic solvents used conventionally in solution-type coating compositions. Examples of suitable organic solvents include aromatic hydrocarbon solvents such as toluene, xylene and the like, olefin compounds, cycloolefin compounds, naphthas, alcohols such as methyl, ethyl, isopropyl and n-butyl alcohols, ketones such as methyl ethyl ketone and methyl isobutyl ketone, esters such as ethyl acetate and butyl acetate, chlorinated hydrocarbon compounds such as methylene chloride and trichloroethylene, glycol ethers such as ethylene glycol monoethyl ether and ethylene glycol monobutyl ether, glycol monoether monoesters such as ethylene glycol monomethyl ether acetate and ethylene glycol monoethyl ether acetate and so on.

The coating composition of the present invention can be prepared in a method undertaken for the preparation of conventional coating compositions of the respective types. The coating composition of the invention can be applied to any substrate material including, for example, metal, wood, plastic, glass, ceramic and the like without particular limitations. The coating method is also not particularly limitative and any of conventional coating methods can be undertaken including, for example, air-spray coating, airless coating, electrostatic coating, roll-coater coating and the like. The coating works can be performed by a one-coat method, two-coat method and so on depending on the intended application of the coated articles.

In the next place, a description is given of the inventive ink compositions.

The ink composition of the present invention contains, as a coloring agent, the above described chromatic-color metal flake pigment in an amount in the range from 0.1 to 70% by weight based on the film-forming constituent of the ink. Various kinds of film-forming materials can be used for the purpose without particular limitation as being selected from those used in conventional ink compositions. Examples of suitable film-forming materials include, for example, synthetic resins such as phenolic resins, alkyd resins, polyamide resins, acrylic resins, urea resins, melamine resins and polyvinyl chloride resins, natural resins such as resin and Gilsonite, cellulose derivatives and vegetable oils such as linseed oil, tung oil and soybean oil. It is optional to use two kinds or more of these film-forming materials in combination according to the intended application of the ink composition.

The ink composition of the present invention essentially contains the above described chromatic-color metal flake pigment in an amount in the range from 0.1 to 70% by weight based on the above named film-forming material of ink. When the amount of the pigment in the ink composition is too small, the desired aesthetic coloring effect can hardly be obtained. When the amount of the pigment is too large in the ink composition, on the other hand, the practical usefulness of the ink composition is decreased with poor workability in printing. It is optional in the ink composition of the present invention that the above described chromatic-color metal flake pigment is used in combination with colored pigments of other types conventionally used in ink compositions with an object of further enhancing the aesthetic coloring effect.

In addition to the above described film-forming material, chromatic-color metal flake pigment and colored pigments optionally added according to need, the ink composition of the present invention can be admixed with various kinds of additives conventionally used in ink compositions such as waxes, plasticizers, dispersing agents and the like according to need. Further, the type of the inventive ink composition is not particularly limitative including the types of a solution in an organic solvent, aqueous solution and aqueous emulsion.

When the inventive ink composition is of the type of a solution in an organic solvent, various kinds of organic solvents can be used therefor without particular limitations as being selected from those used in conventional solution-type ink compositions. Examples of suitable organic solvents include, for example, aromatic hydrocarbon solvents such as toluene and xylene, olefin compounds, cycloolefin compounds, naphthas, alcohols such as methyl, ethyl, isopropyl and n-butyl alcohols, ketones such as methyl ethyl ketone and methyl isobutyl ketone, esters such as ethyl acetate and butyl acetate, chlorinated hydrocarbon compounds such as methylene chloride and trichloroethylene, glycol ethers such as ethylene glycol monoethyl ether and ethylene glycol monobutyl ether, glycol monoether monoesters such as ethylene glycol monomethyl ether acetate and ethylene glycol monoethyl ether acetate and so on.

The inventive ink composition can be prepared in a conventional method undertaken in the preparation of prior art ink compositions of the respective types. The ink composition of the invention can be used in printing works in a manner conventionally undertaken.

A description is given below of the cosmetic preparations of the invention.

The cosmetic preparation of the present invention essentially contains the chromatic-color metal flake pigment as a coloring agent in an amount from 5 to 50% by weight based on the overall amount of the composition. The other ingredients of the cosmetic preparation than the pigment are not particularly limitative and any of the materials used in conventional cosmetic preparations can be the constituents of the inventive composition. Examples of such materials include vegetable and animal oils such as linseed oil, sunflower seed oil, olive oil, castor oil, camellia oil, yolk oil and turtle oil, waxes such as sperm oil, beeswax, spermaceti wax, lanolin, carnauba wax, montan wax and candelilla wax, paraffinic hydrocarbons, fatty acids such as stearic acid and oleic acid as well as derivatives thereof, higher alcohols such as lauryl alcohol, stearyl alcohol, lanolin alcohol, hydrogenated lanolin alcohol and hexyl decanol and so on.

The cosmetic preparation of the invention contains the above described chromatic-color metal flake pigment in an amount from 0.1 to 50% by weight or, preferably, from 0.5 to 30% by weight based on the overall amount of the composition. When the amount of the pigment is too small, the desired aesthetic coloring effect can hardly be obtained. When the amount of the pigment is too large, on the other hand, the composition cannot be applied smoothly to the human skin. It is optional that the cosmetic preparation of the invention can be compounded with the chromatic-color metal flake pigment as combined with colored pigments of other types conventionally used in cosmetic preparations with an object of further enhancing the aesthetic coloring effect.

The cosmetic preparations of the invention include makeup cosmetics, e.g., rouges, eye shadows and manicure enamels, and foundations in the form of a liquid cream, paste, powder cake or stick without particular limitations. These cosmetic compositions can be prepared in a method conventionally undertaken in the industry of cosmetics.

Following is a description of the molding compound of plastic resin according to the invention.

The inventive molding compound of plastic resin contains the chromatic-color metal flake pigment in an amount in the range from 0.1 to 50% by weight based on the overall amount of the molding compound. The plastic resin as the principal ingredient of the inventive molding compound is not particularly limitative and any plastic resins used in the prior art for molding of shaped articles can be used here. Examples of the plastic resins include polyvinyl chloride resins, plasticized polyvinyl chloride resins, polyethylene resins, polypropylene resins, ABS resins, phenolic resins, polyamide resins, alkyd resins, urethane resins, melamine resins and the like.

It is essential that the inventive molding compound of plastic resin contains the chromatic-color metal flake pigment in an amount in the range from 0.1 to 50% by weight based on the overall amount of the molding compound. When the amount of the pigment is too small, the desired aesthetic coloring effect can hardly be obtained in the molding compound or the shaped articles molded thereof. When the amount of the pigment is too large, on the other hand, the molding workability of the molding compound may be somewhat decreased.

It is optional that the inventive molding compound of plastic resin is compounded with the chromatic-color metal flake pigment as combined with colored pigments of other types with an object of further enhancing the aesthetic coloring effect. The inventive molding compound of plastic resin may optionally contain various kinds of fillers and other additives conventionally used in molding compounds of plastic resins in the prior art.

Various forms of shaped articles can be prepared from the inventive molding compound of plastic resin by a known method such as extrusion molding and injection molding.

In the following, examples are given to illustrate the present invention in more detail but not to limit the scope of the invention in any way.

EXAMPLE 1

A suspension of metal flakes was prepared by adding 3.9 g of titanium metal flakes (ALPASTE-62-1175, a product by Toyo Aluminum Co.) after four times washing with acetone to a mixture of 68.9 g of isopropyl alcohol and 2.2 g of water under agitation. The suspension had a pH of 5. Into this suspension kept at 25° C. with agitation was added dropwise a mixture of 21.6 g of isopropyl alcohol and 3.4 g of tetraisopropoxy titanium (A-1, a product by Nippon Soda Co.) over a period of 5 hours. The rate of addition of the organic titanate ester to the suspension was $4.9 \times 10^{-6}$ moles/minute per square meter of the surface area of the metal flakes.

After completion of the dropwise addition of the titanate ester solution, the suspension was further agitated for additional one hour at the same temperature followed by filtration to recover the metal flakes which were calcined by heating at 350° C. for 1 hour in an atmosphere of argon gas.

The thus obtained chromatic-color metal flake pigment was blue in color and exhibited silky luster with little glaringness as in conventional metal flake pigments.

Table 1 below summarizes the formulation of the reaction mixture and the conditions of the preparation.

EXAMPLES 2 TO 10

The procedure in each of these Examples was similar to Example 1 except for modifications in the formulation of the reaction mixture and the conditions of the preparation as is summarized in Table 1. 4 in Example 2 and the pH value was 5 in each of the other Examples and the calcination temperature was always 350° C. The molar ratio of water added to the reaction mixture to the titanate ester was 10 in each Example except for Example 9 where the molar ratio was 48.

Following are the characterization data of the metal flakes and the organic titanate esters appearing in Table 1 and Table 2.

1) Titanium flakes: ALPASTE-62-1175, a product by Toyo Aluminum Co., having an average particle diameter of 20 μm and a thickness of the flakes of 1 μm 2) Aluminum flakes: ALPASTE-1810YL, a product by Toyo Aluminum Co., having an average particle diameter of 20 μm and a thickness of the flakes of 0.4 μm 3) Bronze flakes: BRONZE POWDER BS-11303-G1657, a product by Toyo Aluminum Co., having an average particle diameter of 25 μm and a thickness of the flakes of 1 μm 4) Stainless steel flakes: SP Ace SUS 304, a product by Kawatetsu Technoresearch Co., having an average particle diameter of 30 μm and a thickness of the flakes of 0.5 μm 5) Organic titanate ester A-1: tetraisopropoxy titanium, a product by Nippon Soda Co.

6) Organic titanate ester B-1: tetra-n-butoxy titanium, a product by Nippon Soda Co.

7) Organic titanate ester B-10: partial hydrolysis-condensation product of tetra-n-butoxy titanium having a degree of polymerization of 10, a product by Nippon Soda Co.

TABLE 1

| Example No. | 1 | 2 | 3 | 4 | 5 | 6 | 7 | 8 | 9 | 10 |
|---|---|---|---|---|---|---|---|---|---|---|
| Formulation, % by weight | | | | | | | | | | |

TABLE 1-continued

| Example No. | 1 | 2 | 3 | 4 | 5 | 6 | 7 | 8 | 9 | 10 |
|---|---|---|---|---|---|---|---|---|---|---|
| Metal flakes | | | | | | | | | | |
| Titanium[1] | 3.9 | 6.5 | 4.6 | — | — | — | — | 6.5 | 30.7 | — |
| Aluminum[2] | — | — | — | 3.4 | 0.7 | — | — | — | — | 3.4 |
| Bronze[3] | — | — | — | — | — | 3.9 | — | — | — | — |
| Stainless steel[4] | — | — | — | — | — | — | 2.0 | — | — | — |
| Titanate ester | | | | | | | | | | |
| A-1[5] | 3.4 | 3.4 | 3.4 | 2.7 | 2.6 | 3.4 | 2.8 | — | — | — |
| B-1[6] | — | — | — | — | — | — | — | 4.1 | — | — |
| B-10[7] | — | — | — | — | — | — | — | — | 17.2 | 2.9 |
| Water | 2.2 | 2.1 | 2.2 | 1.7 | 1.7 | 2.2 | 1.8 | 2.1 | 6.7 | 1.2 |
| Isopropyl alcohol | 90.5 | 88.0 | 89.8 | 92.2 | 95.0 | 90.5 | 93.4 | 87.3 | 45.4 | 92.5 |
| Total | 100.0 | 100.0 | 100.0 | 100.0 | 100.0 | 100.0 | 100.0 | 100.0 | 100.0 | 100.0 |
| Conditions of preparation | | | | | | | | | | |
| Concentration of titanate ester, moles/liter | 0.1 | 0.1 | 0.1 | 0.08 | 0.08 | 0.1 | 0.08 | 0.1 | 0.1 | 0.1 |
| Temperature of hydrolysis, °C. | 25 | 25 | 50 | 40 | 25 | 25 | 25 | 50 | 50 | 70 |
| Rate of titanate ester addition, moles/min.m$^2$ | $4.9 \times 10^{-6}$ | $8.8 \times 10^{-6}$ | $1.73 \times 10^{-5}$ | $2.1 \times 10^{-6}$ | $1.1 \times 10^{-5}$ | $2.3 \times 10^{-5}$ | $1.3 \times 10^{-5}$ | $6.17 \times 10^{-6}$ | $8.36 \times 10^{-6}$ | $6.1 \times 10^{-7}$ |
| Color tone of product pigment | Blue | Golden | Purple | Golden | Blue | Green | Blue | Golden | Purple | Blue |

EXAMPLE 11

A suspension of metal flakes was prepared by adding 3.9 g of the same titanium flakes as used in Example 1 after four times washing with acetone to a mixture of 3.4 g of tetraisopropoxy titanium (A-1, supra) and 68.9 g of isopropyl alcohol. The concentration of the organic titanate ester in the suspension was 0.1 mole/liter and the suspension had a pH of 5. A mixture of 2.2 g of water and 21.6 g of isopropyl alcohol was added dropwise to the suspension under agitation at 25° C. over a period of 5 hours.

After completion of the dropwise addition of the aqueous isopropyl alcohol, the suspension was further agitated for additional 1 hour at room temperature and then filtered to recover the titanium flakes. The metal flake pigment was dried and calcined by heating at 350° C. for 1 hour in an atmosphere of argon gas. The thus obtained chromatic-color metal flake pigment was blue in color exhibiting silky luster with little glaringness as in conventional metal flake pigments.

Table 2 below summarizes the formulation of the reaction mixture and the conditions of the preparation.

EXAMPLES 12 TO 20

The procedure in each of these Examples was substantially the same as in Example 11 except for modification of the types and amounts of the metal flakes and the organic titanate ester as is summarized in Table 2. Table 2 also shows the colors of the thus prepared chromatic-color metal flake pigments. The suspensions always had a pH of 5 excepting Example 12 in which the pH of the suspension was 4. The molar ratio of water to the organic titanate ester was always 10 and the temperature of calcination was always 350° C. in these Examples.

TABLE 2

| Example No. | 11 | 12 | 13 | 14 | 15 | 16 | 17 | 18 | 19 | 20 |
|---|---|---|---|---|---|---|---|---|---|---|
| Formulation, % by weight | | | | | | | | | | |
| Metal flakes | | | | | | | | | | |
| Titanium[1] | 3.9 | 6.5 | 4.6 | — | — | — | — | 6.5 | 3.9 | 30.7 |
| Aluminum[2] | — | — | — | 3.4 | 0.7 | — | — | — | — | — |
| Bronze[3] | — | — | — | — | — | 3.9 | — | — | — | — |
| Stainless steel[4] | — | — | — | — | — | — | 2 | — | — | — |
| Titanate ester | | | | | | | | | | |
| A-1[5] | 3.4 | 3.4 | 3.4 | 2.7 | 2.6 | 3.4 | 2.8 | — | — | — |
| B-1[6] | — | — | — | — | — | — | — | 4.1 | 4.1 | — |
| B-10[7] | — | — | — | — | — | — | — | — | — | 17.2 |
| Water | 2.2 | 2.1 | 2.2 | 1.7 | 1.7 | 2.2 | 1.8 | 2.1 | 2.2 | 6.7 |
| Isopropyl alcohol | 90.5 | 88.0 | 89.8 | 92.2 | 95.0 | 90.5 | 93.4 | 87.3 | 45.4 | 92.5 |
| Total | 100.0 | 100.0 | 100.0 | 100.0 | 100.0 | 100.0 | 100.0 | 100.0 | 100.0 | 100.0 |
| Conditions of preparation | | | | | | | | | | |
| Concentration of titanate ester, moles/liter | 0.1 | 0.1 | 0.1 | 0.08 | 0.08 | 0.1 | 0.08 | 0.1 | 0.1 | 0.1 |
| Temperature of hydrolysis, °C. | 25 | 25 | 50 | 40 | 25 | 25 | 25 | 50 | 50 | 25 |
| Rate of titanate ester addition, moles/min.m$^2$ | $3.3 \times 10^{-2}$ | $3.3 \times 10^{-2}$ | $3.3 \times 10^{-2}$ | $3.3 \times 10^{-2}$ | $1.7 \times 10^{-2}$ | $8.3 \times 10^{-2}$ | $1.7 \times 10^{-1}$ | $3.3 \times 10^{-2}$ | $3.3 \times 10^{-2}$ | $8.1 \times 10^{-2}$ |
| Color tone of product pigment | Blue | Golden | Purple | Golden | Blue | Green | Blue | Golden | Blue | Purple |

COMPARATIVE EXAMPLE

An attempt was made to prepare a pigment of titanium oxide coated titanium flakes with titanyl sulfate as the starting material according to the procedure disclosed in Japanese Patent Publication 43-25644 which was a method conventionally undertaken for the preparation of a pearlescent pigment.

Thus, 19.7 g of titanium metal flakes after four times washing with acetone were suspended in an aqueous solution of 10.3 g of titanyl sulfate dihydrate containing 30% by weight of $TiO_2$ (T-M crystals, a product by Teikoku Kako Co.) in 70.0 g of water and the suspension was heated to be rapidly brought to a boiling condition. After about 2.5 hours of continued boiling under reflux, the metal flakes were recovered by filtration followed by washing with water. The result was that no pigment could be obtained because the titanium flakes had been completely dissolved in the strongly acidic aqueous medium having as pH of 3 or below.

REFERENCE EXAMPLE

Each 2.0 g portion of the chromatic-color metal flake pigments prepared in Examples 1 to 20 and four kinds of the metal flakes used as the base materials in Examples 1 to 20 was taken in a test tube, into which 30 ml of 1N hydrochloric acid were added and the flakes were dispersed therein by applying ultrasonic waves followed by standing as such for 24 hours at room temperature to test the resistance of the metal flakes against acid. The results ware that the pigments prepared in Examples were all very stable without noticeable changes excepting the pigments prepared in Examples 3, 4, 14 and 15 which were found to have been slightly dissolved in the acid while the metal flakes before the coating treatment were completely dissolved.

As is understood from the above given results, the pigments prepared in Examples 1 to 20 each had high hue and chroma as compared with conventional metal flake pigments with a color tone somewhat differing depending on the metal of the base flakes and exhibited silky luster free from glaringness as in conventional metal flake pigments. Furthermore, the chromatic-color metal flake pigments of the invention had much higher resistance against acid than conventional untreated metal flakes.

Following are the examples to illustrate the coating compositions compounded with the above described chromatic-color metal flake pigment.

EXAMPLE 21

A base-coat coating composition according to the invention was prepared first by blending 733 g of an acrylic resin (Acrydic A-47-712, a product by DAINIPPON INK AND CHEMICALS INCORPORATED) containing 50% by weight of non-volatile matter, 15.7 g of a melamine resin (Cymel 303, a product by Mitsui-Toatsu Chemical Co.), 10.4 g of the chromatic-color metal flake pigment prepared in Example 1, 0.3 g of p-toluene sulfonic acid and 0.3 g of an ultraviolet absorber (Tinuvin 900, a product by Ciba Geigy) for 30 minutes in a dissolver and then diluting the thus prepared blend with a thinner which was a 7:2:1 by weight mixture of toluene, isobutyl acetate and isobutyl alcohol to such an extent that the resultant diluted blend has a viscosity of 15 seconds as measured with a #4 Ford cup. On the other hand, a clear-coat coating composition was prepared by first blending 81.9 g of an acrylic resin (Acrydic A-44-179, a product by DAINIPPON INK AND CHEMICALS INCORPORATED) containing 50% by weight of non-volatile matter, 17.5 g of a melamine resin (Cymel 303, supra), 0.3 g of p-toluene sulfonic acid and 0.3 g of an ultraviolet absorber (Tinuvin 900, supra) for 30 minutes in a dissolver and then diluting the thus prepared blend with a thinner which was a 9:1 by weight mixture of Solvesso #100 (a product by Esso Chemical Co.) and butyl alcohol to such an extent that the resultant diluted blend had a viscosity of 25 seconds as measured with a #4 Ford cup.

In the next place, a test panel coated with a sealer was coated with the above prepared base-coat coating composition by air spraying in a coating thickness of 15 μm as dried and, after standing as such for 15 minutes at 25° C., overcoated with the clear-coat coating composition by air spraying in a coating thickness of 25 μm as dried. After standing as such for 15 minutes at 25° C., the coated panel was baked at 140° C. for 30 minutes to cure the coating film. The thus obtained coating film was blue in color exhibiting silky luster.

EXAMPLE 22

A coating composition was prepared by first blending 60.2 g of an alkyd resin (Vernoc DE-140-70, a product by DAINIPPON INK AND CHEMICALS INCORPORATED) containing 70% by weight of non-volatile matter and 26.3 g of the chromatic-color metal flake pigment of purple color obtained in Example 3 for 30 minutes in a dissolver followed by the addition of 22.5 g of an isocyanate compound (Vernoc DN-950, a product by DAINIPPON INK AND CHEMICALS INCORPORATED) containing 75% by weight of non-volatile matter and then diluting the blend with a thinner which was a 1:9 by weight mixture of xylene and Solvesso #100 (supra) to such an extent that the resultant diluted blend had a viscosity of 25 seconds as measured with a #4 Ford cup.

In the next place, a test panel coated with a sealer was coated with this coating composition by air spraying in a coating thickness of 35 μm as dried followed by baking at 80° C. for 30 minutes to cure the coating film. The thus formed coating layer was purple in color exhibiting silky luster.

EXAMPLE 23

A water-soluble base-coat coating composition was prepared by mixing 69.5 g of an acrylic resin (Paraloid WR-97, a product by Rohm and Haas Co.) containing 70% by weight of non-volatile matter after neutralization with triethanolamine, 20.8 g of a melamine resin (Cymel 303, supra) and 7.0 g of the chromatic-color metal flake pigment prepared in Example 4 and agitating the mixture for 10 minutes in a dissolver followed by dilution of the mixture with water to such an extent that the resultant diluted mixture had a viscosity of 20 seconds as measured with a #4 Ford cup.

In the next place, a test panel coated with a sealer was coated with this base-coat coating composition by air spraying in a coating thickness of 15 μm as dried followed by setting at 50° C. for 10 minutes and baking at 160° C. for 30 minutes, thereafter, the coated surface was overcoated with the clear coating composition prepared in Example 21 by air spraying in a coating thickness of 25 μm as dried followed by baking at 140° C. for 30 minutes to give a finished coating film which was golden in color exhibiting silky luster.

Following are the examples to illustrate the ink composition of the present invention.

EXAMPLE 24

An ink composition was prepared by uniformly blending 10 parts by weight of the chromatic-color metal flake pigment prepared in Example 4, 20 parts by weight of barium sulfate, 44.8 parts by weight of an acrylic resin (Resin QR-1074, a product by Rohm and Haas Co.) containing 75% by weight of non-volatile matter, 14.4 parts by weight of a melamine resin (Cymel 303, supra), 3.2 parts by weight of xylene and 7.6 parts by weight of ethylene glycol monoethyl ether acetate in a dissolver for 30 minutes. A tinplate was printed with this ink composition by the method of screen printing. The thus obtained printed surface was golden in color exhibiting silky luster.

EXAMPLE 25

An ink composition was prepared by admixing 40.4 parts by weight of a hexamethylene diisocyanate derivative as a curing agent (Coronate EH, a product by Nippon Polyurethane Industry Co.) with 100 parts by weight of a base composition composed of 20% by weight of the chromatic-color metal flake pigment prepared in Example 5, 48% by weight of a polyester resin (DESMOPHEN 670, a product by Sumitomo Bayer Urethane Co., LTD.), 20% by weight of barium sulfate, 0.1% by weight of dibutyl tin dilaurate as a catalyst, 3.6% by weight of xylene and 8.3% by weight of ethylene glycol monoethyl ether acetate.

A tinplate was printed with this ink composition by the method of screen printing. The thus obtained printed surface was blue in color exhibiting silky luster.

Following are the examples to illustrate the cosmetic preparations of the present invention.

EXAMPLE 26

A powdery eye shadow was prepared by uniformly blending 32 parts by weight of talc, 10 parts by weight of zinc stearate, 52.5 parts by weight of the chromatic-color metal flake pigment prepared in Example 5, 5.0 parts by weight of liquid paraffin, 0.3 part by weight of glycerin monostearate and 0.2 part by weight of a perfume. The thus prepared eye shadow was blue in color and, when applied to human skin, exhibited silky luster.

EXAMPLE 27

A creamy foundation was prepared by uniformly blending 15 parts by weight of talc, 7 parts by weight of sericite, 5 parts by weight of titanium dioxide, 3 parts by weight of the chromatic-color metal flake pigment prepared in Example 6, 15 parts by weight of liquid paraffin, 2 parts by weight of ethylene glycol, 15 parts by weight of ethyl alcohol, 38 parts by weight of water and small amounts of a perfume and antiseptic agent. This foundation was green in color and, when applied to human skin, exhibited silky luster of high aesthetic value not obtained with any conventional creamy foundations.

Following is an example to illustrate the molding compound of plastic resin according to the invention.

EXAMPLE 28

A blend composed of 3.8 parts by weight of the chromatic-color metal flake pigment prepared in Example 5 and 96.3 parts by weight of an ABS resin was prepared by blending in a dissolver for 5 minutes and then introduced into an extrusion molding machine to give a shaped article of the molding resin compound. This shaped article was blue in color exhibiting silky luster.

As is understood from the above given description, the chromatic-color metal flake pigments of the present invention can exhibit various colors by adequately controlling the thickness of the coating layer of titanium oxide formed on the surface of the base metal flakes. The hiding power of the inventive pigment is equivalent to that of conventional metal flake pigments of aluminum, bronze and the like as a result of the use of metal flakes as the base material.

The chromatic-color metal flake pigment of the invention exhibits an iridescent color tone delicately varying depending on the angle of incident light and view angle without glaringness as in conventional metal flake pigments so that the inventive pigment can give very aesthetic decorativeness of silky feeling capable of giving a high-class atmosphere not obtained with conventional pigments.

Moreover, the chromatic-color metal flake pigment of the invention has high chemical stability by virtue of the chemically inert coating layer of titanium oxide formed on the surface of the base metal flakes exhibiting high resistance against chemicals and water so that the inventive pigments can be used in water-borne metallic coating compositions in which conventional aluminum flake pigments and the like can hardly be used in respect of the durability.

When the chromatic-color metal flake pigment of the invention is used as a coloring agent of coating compositions, ink compositions, cosmetic preparations, molding compounds of plastic resins and the like, highly aesthetic decorativeness of silky feeling is obtained to give a high-class atmosphere not obtained by using any conventional pigments.

What is claimed is:

1. A chromatic-color metal flake pigment which comprises:
   (a) flakes of a metal selected from the group consisting of aluminum, bronze, stainless steel, tin and iron; and
   (b) a coating layer of titanium oxide on the surface of the metal flakes formed by hydrolyzing a hydrolyzable organic titanate ester compound and depositing the titanium oxide on said surface,
   wherein the coating layer has a thickness of 40 nm to 155 nm and the hydrolyzable organic titanate ester compound is of the formula

in which R is an alkyl group having 2 to 10 carbon atoms and the subscript n is a positive integer not exceeding 10 and
   wherein the hydrolyzable organic titanate ester compound is hydrolyzed in an organic medium having a pH from 4 to 8.

2. The chromatic-color metal flake pigment as claimed in claim 1 wherein the metal flakes have an average particle diameter from 1 to 100 $\mu$m and a thickness from 0.01 to 20 $\mu$m.

3. A coating composition which comprises a film forming resin and as a coloring agent, from 0.1 to 70% by weight, based on the film-forming resin, of a chromatic-color metal flake pigment according to claim 1.

4. The coating composition as claimed in claim 3, wherein the film-forming resin is selected from the group consisting of acrylic resins, polyester resins, resin mixtures of an acrylic resin and cellulose acetate butyrate, alkyd resins, urethane resins, epoxy resins, silicone resins, polyamide resins, epoxy-modified alkyd resins, phenolic resins and mixtures thereof.

5. An ink composition which comprises a film-forming ingredient and as a coloring agent, from 0.1 to 70% by weight, based on the film-forming ingredient, of a chromatic-color metal flake pigment according to claim 1.

6. The ink composition as claimed in claim 5, wherein the film-forming ingredient is selected from the group consisting of phenolic resins, alkyd resins, polyamide resins, acrylic resins, urea resins, melamine resins, polyvinyl chloride resins, Gilsonite, linseed oil, tung oil, soybean oil mixtures thereof.

7. A cosmetic preparation which comprises from 0.1 to 50% by weight of a chromatic-color metal flake pigment according to claim 1 based on the overall amount of the preparation.

8. The cosmetic composition as claimed in claim 7 which further comprises an additional ingredient selected from the group consisting of linseed oil, sunflower seed oil, olive oil, castor oil, camellia oil, yolk oil, turtle oil, sperm oil, beeswax, spermaceti wax, lanolin, carnauba wax, montan wax, candelilla wax, stearic acid, oleic acid, lauryl alcohol, stearyl alcohol, lanolin alcohol, hexyl decanol and mixtures thereof.

9. A molding compound comprising a plastic resin and as a coloring agent, from 0.1 to 50% by weight of a chromatic-color metal flake pigment according to claim 1, based on the overall amount of the compound.

10. The chromatic-color metal flake pigment as claimed in claim 1 wherein the hydrolyzable organic titanate ester compound is selected from the group consisting of tetra-isopropoxy titanium, tetra-n-butoxy titanium, tetrakis (2-ethylhexoxy) titanium, tetra-n-pentoxy titanium, tetra-n-hexoxy titanium, tetra-n-heptoxy titanium and tetra-n-octoxy titanium.

11. The chromatic-color metal flake as claimed in claim 1 wherein the organic medium is an organic solvent selected from the group consisting of a monohydric lower alcohol having 1 to 6 carbon atoms, benzene, toluene, xylene and mixtures thereof.

12. The chromatic-color metal flake pigment as claimed in claim 11 wherein the concentration of the hydrolyzable titanate ester in the organic medium is from 0.001 to 1 mole/liter.

13. The chromatic-color metal flake pigment as claimed in claim 1 wherein at least 2 moles of water per mole of said organic titanate ester compound are added during said hydrolyzing.

14. The chromatic-color metal flake pigment as claimed in claim 1 wherein the coating layer comprises one coating.

* * * * *